United States Patent [19]
Lin

[11] Patent Number: 5,731,480
[45] Date of Patent: Mar. 24, 1998

[54] COPRODUCTION OF VINYLIDENE ALCOHOLS AND VINYLIDENE HYDROCARBONS

[75] Inventor: Kaung-Far Lin, Baton Rouge, La.

[73] Assignee: Albemarle Corporation, Richmond, Va.

[21] Appl. No.: 552,638

[22] Filed: Nov. 3, 1995

[51] Int. Cl.⁶ .................................................. C07C 29/04
[52] U.S. Cl. ........................... 568/897; 556/185; 556/190; 585/328; 585/532; 585/533; 585/637
[58] Field of Search ........................... 556/185, 190; 585/328, 532, 533, 637; 568/897

[56] References Cited

U.S. PATENT DOCUMENTS

| | | | |
|---|---|---|---|
| 3,346,662 | 10/1967 | Antonsen | 260/683.15 |
| 3,887,624 | 6/1975 | Gipson et al. | 260/615 B |
| 3,952,068 | 4/1976 | Gipson et al. | 260/632 R |
| 4,032,582 | 6/1977 | Trebillon | 568/911 |
| 4,658,078 | 4/1987 | Slaugh et al. | 585/512 |
| 4,973,788 | 11/1990 | Lin et al. | 585/511 |
| 5,087,788 | 2/1992 | Wu | 585/512 |
| 5,157,190 | 10/1992 | Lin et al. | 585/512 |

*Primary Examiner*—C. Warren Ivy
*Assistant Examiner*—Garth M. Dahlen
*Attorney, Agent, or Firm*—Philip M. Pippenger

[57] ABSTRACT

A process is described for coproducing vinylidene alcohol and vinylidene olefin. The process involves dimerizing one or more vinylolefins with an alkyl aluminum catalyst to form a first product mixture comprising at least vinylidene olefin and alkyl aluminum compound. The vinylidene olefin is then reacted with the alkyl aluminum compound under displacement conditions to form 1-olefin while concurrently removing the 1-olefin from the displacement reaction mixture to form a second product mixture comprising at least beta-branched alkyl aluminum compound. The second product mixture is treated with air or oxygen under mild oxidation conditions to form a third product mixture comprising at least beta-branched aluminum alkoxide. The beta-branched aluminum alkoxide is then hydrolyzed to form vinylidene alcohol. The process makes effective use of the alkyl aluminum catalyst both as a catalyst and as a reactant, and requires only a relatively small amount of reaction equipment.

30 Claims, No Drawings

COPRODUCTION OF VINYLIDENE ALCOHOLS AND VINYLIDENE HYDROCARBONS

TECHNICAL FIELD

This invention relates to a process whereby two useful products, namely one or more vinylidene alcohols and one or more vinylidene hydrocarbons, are coproduced from a vinylolefin.

GLOSSARY

As used herein the following terms, whether singular or plural and whether capitalized or not, have the following meanings:

"Vinylolefin" is an olefin having the structure $R^1\text{—CH=CH}_2$.

"Linear 1-olefin" is vinylolefin in which there is no branch in the carbon chain.

"Branched olefin" is a 1-olefin having at least one branch in the chain.

"Vinylidene olefin" is a branched olefin having the structure $(R^1)(R^2)\text{C=CH}_2$.

"Trisubstituted olefin" is an internal olefin having the structure $(R^1)(R^2)\text{C=CHR}^3$.

"Deep internal olefin" is a linear olefin in which the double bond is between two carbon atoms each of which is at least the fourth carbon atom away from either end of the chain.

"Vinylidene alcohol" is an alcohol having the structure $(R^1)(R^2)\text{CHCH}_2\text{OH}$ "Linear alkyl aluminum" is an aluminum alkyl in which substantially all of the alkyl groups are straight chain primary alkyl groups having at least two carbon atoms each.

"Branched alkyl aluminum" is an aluminum alkyl in which there is a branch in at least one alkyl group.

In the above formulas $R^1$, $R^2$ and $R^3$ are alkyl groups which can be the same or different.

BACKGROUND

Vinylidene alcohols, often referred to as Guerbet alcohols, have achieved commercial importance because of their "double tail" structure. They find use in the manufacture of surfactants, detergents, lubricant additives, and other finished products. Traditionally, these alcohols have been made by the Guerbet synthesis wherein a normal primary alcohol is reacted with a sodium alkoxide in the presence of a nickel catalyst. The resultant alcohol has a linear branch on the beta-carbon atom.

Vinylidene olefins are also of commercial importance as raw materials for use in producing-double tailed oxo alcohols and other functionalized derivatives.

A welcome contribution to the art would be the provision of an efficient and highly economical process by which both vinylirene alcohols and vinylidene olefins can be coproduced with a minimum of process equipment. This invention is believed to constitute such a contribution.

SUMMARY OF THE INVENTION

In accordance with one of its embodiments, this invention provides a multistage process for the coproduction of at least one vinylidene alcohol and at least one vinylidene olefin. The process comprises (a) dimerizing one or more vinylolefins with an alkyl aluminum catalyst under dimerization conditions to form a first product mixture comprising at least vinylidene olefin and aluminum alkyl compound; (b) reacting vinylidene olefin with the aluminum alkyl compound under displacement conditions to form displaced 1-olefin and concurrently removing such 1-olefin from the displacement reaction mixture to form a second product mixture comprising at least beta-branched alkyl aluminum compound (residual vinylidene olefin is typically present as well); (c) treating the second product mixture with air or oxygen under mild oxidation conditions to form a third product mixture comprising at least beta-branched aluminum alkoxide; and (d) hydrolyzing the beta-branched aluminum alkoxide to form vinylidene alcohol.

It will be seen that the process takes full advantage of the aluminum alkyl employed as the dimerization catalyst in the first step. That is, the aluminum alkyl not only serves as the catalyst in the dimerization reaction, but is a reactant in the displacement step, the precursor of the aluminum reactant in the oxidation step and the precursor of the aluminum reactant in the hydrolysis step. And if desired, the aluminum values from the hydrolysis can be converted to alumina, alum, metal aluminates such as sodium aluminate, etc., for other uses.

In a preferred embodiment of this invention, the process comprises the following steps:

a) dimerizing a vinylolefin (most preferably a linear 1-olefin) with an alkyl aluminum catalyst (preferably a linear alkyl aluminum catalyst) under dimerization conditions to form a first product mixture comprising (i) as dimerized products, vinylidene olefin and deep internal olefin, and (ii) as other components, linear or branched aluminum alkyl and monomeric olefin monomer;

b) subjecting the first product mixture to olefin displacement conditions whereby vinylidene olefin displaces alkyl groups from the aluminum alkyl as displaced linear or branched 1-olefin which is removed from the reaction mixture substantially as soon as it is formed, to form a second product mixture comprising beta-branched alkyl aluminum, deep internal olefin and residual vinylidene olefin;

c) treating the second product mixture with air or oxygen under mild oxidation condition to form a third product mixture comprising beta-branched aluminum alkoxide, deep internal olefin and residual vinylidene olefin;

d) distilling the third product mixture to recover the vinylidene olefin and the deep internal olefin as the distillate leaving beta-branched aluminum alkoxide in the distillation residue; and e) hydrolyzing the beta-branched aluminum alkoxide in an aqueous medium to form vinylidene alcohol which is recovered from the aqueous hydrolysis medium.

The process of this invention requires only a relatively small mount of process equipment in that a number of the operations can be conducted in the same reaction vessel. For example, the dimerization, displacement, oxidation and distillation steps can be performed in a single reactor such as a glass-lined reactor equipped with suitable distillation auxiliaries. Unless the olefin feed in the initial dimerization reaction is a mixture having a broad distillation range, the distillation equipment can be very simple in design and construction because the separations in which it is used will not contain materials having close boiling points. For example if 1-octene is dimerized using trioctylaluminum catalyst, the olefins in the system are primarily a combination of $C_8$ and $C_{16}$ olefins which are readily separated by distillation. The hydrolysis is preferably conducted in a stainless steel vessel, and if desired, the recovery of the vinylidene alcohol can also be carried out using that same vessel, such as by a decantation phase separation.

The above and other embodiments of this invention will become still further apparent from the ensuing description and appended claims.

Dimerization

The vinylolefins which are subjected to the dimerization step typically have at least 3 and preferably at least 4 carbon atoms per molecule and can be individual olefins or mixtures of two or more such olefins. Preferred olefins are linear (i.e., straight chain) olefins typified by such compounds as propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, and analogous higher homologs which may contain up to about 36 carbon atoms, but more preferably, no more than about 24 carbons atoms, and still more preferably no more than about 18 carbons atoms. Linear 1-olefins having in the range of 4 to about 14 carbon atoms per molecule and mixtures of any two on more such olefins are particularly preferred. Less preferred are branched 1-olefins. Examples include such compounds as 4-methyl-1-pentene, 4-methyl-1-hexene, 5-methyl-1-hexene, 4,5-dimethyl-1-hexene, 5,5-dimethyl-1-hexene, 1-hexene, 4-methyl-1-heptene, 5-methyl-1-heptene, 6-methyl-1-heptene, 5,5-dimethyl-1-heptene, 4,6-dimethyl-1-heptene, and similar branched higher homologs which likewise may contain up to about 36 carbon atoms, but more preferably no more than about 24 carbons atoms, and still more preferably no more than about 18 carbons atoms. It will be understood and appreciated that the 1-olefins which are dimerized in the process can be a mixture of linear and branched 1-olefins. Likewise the 1-olefins used can be in admixture with other hydrocarbons such as paraffinic, cycloparaffinic, and/or aromatic hydrocarbons.

The alkyl aluminum dimerization catalyst is typically one or more trialkyl aluminum compounds in which each alkyl group contains at least two carbon atoms. Examples of such compounds include triethylaluminum, tripropylaluminum, tributylaluminum, tripentylaluminum, trihexylaluminum, tri(4-methylpentyl)aluminum, triheptylaluminum, trioctylaluminum, tri(4-methylheptyl)aluminum, tri(5-methylheptylaluminum, tri(6-methylheptyl)aluminum, tridecylaluminum, tri(4-ethyloctyl)aluminum, tri(6-ethyloctyl)aluminum, tri(6,6-dimethyloctyl)aluminum, tris(dodecyl)aluminum, tris(tetradecyl)aluminum, and the like, including mixtures of compounds of this type. Dialkylaluminum hydrides having at least two carbon atoms in each alkyl group may also be charged as the catalyst, and may in fact react with the 1-olefin to form trialkylaluminum in situ.

In one embodiment the alkyl groups of the catalyst correspond to the vinylolefin to be dimerized. Examples include using tri-n-octylaluminum as catalyst when dimerizing 1-octene, or tri-n-tetradecylaluminum when dimerizing 1-tetradecene. This ensures the formation of a purer dimer product. Similarly, when the vinylolefin is a mixture of two or more vinylolefins which differ in the number of carbon atoms per molecule, an alkyl aluminum catalyst can be used that has the same number of carbon atoms as at least one of the vinylolefins to be dimerized. Preferred mixtures of such olefins include:

a) mixtures of at least two olefins, one of which has n carbon atoms and another of which has n+2 carbon atoms, where n is an integer in the range of from 3 to 34, preferably in the range of from 4 to 22, and more preferably in the range of from 4 to 16;

b) mixtures of at least two olefins, one of which has n carbon atoms and another of which has n+1 carbon atoms, where n is an integer in the range of from 3 to 35, preferably in the range of from 4 to 23, and more preferably in the range of from 4 to 17; and mixtures comprising at least three olefins, one of which has n carbon atoms, another of which has n+1 carbon atoms, and still another of which has n+2 carbon atoms, where n is an integer such that (i) the sum of n+1 is at least 4 and not more than 36, preferably at least 4 and not more than 24, and more preferably at least 4 and not more than 18; and (ii) the sum of n+2 is at least 5 and not more than 36, preferably at least 5 and not more than 24, and more preferably at least 5 and not more than 18.

Another preferred embodiment is a process in which a vinylolefin mixture is dimerized using an alkyl aluminum catalyst which initially is (1) triethylaluminum by itself, or (2) triethylaluminum together with one or a mixture of other alkyl aluminum compounds in which the alkyl groups have more carbon atoms each, (1) being most preferred. In this embodiment, the dimerization catalyst is used with any 1-olefin feed material having 3 to about 36 carbon atoms, preferably 4 to 24 carbon atoms, and more preferably 4 to 18 carbon atoms. This embodiment is advantageous because of the ready availability and low cost of triethylaluminum, and its low molecular weight.

The conditions used in conducting the dimerization include use of substantially anhydrous feed materials and reaction conditions, and use of temperatures in the range of about 100° to about 250° C. (preferably in the range of about 140° to about 200° C.). The proportions of the aluminum alkyl catalyst relative to the olefin being dimerized can be varied over a considerable range. Thus the aluminum alkyl catalyst will typically be used in amounts in the range of about 0.001 to about 1 mol (preferably in the range of about 0.01 to about 0.2 mol) per mol of initial 1-olefin. The reaction is relatively slow at the lower reaction temperatures and lower catalyst concentrations, and is faster when performed at the higher reaction temperatures using the higher catalyst concentrations. Preferably, the reaction is conducted for a period of time sufficient under the conditions employed to convert at least about 80 percent (more preferably at least about 90 percent) of the initial 1-olefin into other products. Experiments have indicated, for example, that the time to achieve 90% conversion at 120° C. may range from about 94 hours using 0.043 mol of aluminum alkyl catalyst per mol of initial vinylolefin up to about 192 hours when using 0.017 mol of aluminum alkyl catalyst per mol of initial vinylolefin. These time periods are presented solely for the purpose of illustration, and do not constitute limitations on the practice of this invention.

Displacement

To perform the displacement reaction the mixture from the dimerization step is subjected either to a thermal displacement reaction or to a catalytic displacement reaction. If a thermal displacement reaction is used, the dimerization reaction mixture is held at a temperature in the range of about 100° to about 300° C. (preferably in the range of about 150° to about 200° C.) while purging the reaction mixture with a sweep of inert gas such as nitrogen, or subjecting the reaction mixture to reduced pressure in the range of about 0.001 to about 200 mm Hg, and preferably in the range of about 0.1 to about 100 mm Hg. In a catalytic displacement reaction a displacement catalyst such as nickel or cobalt is used either in metallic form or preferably as a nickel (II) or cobalt (II) organic compound such as a salt of an organic acid or a complex of an organic chelating agent. Temperatures for catalytic displacement typically fall in the range of about 20° to about 150° C., and preferably in the range of about 40° to about 100° C.

In the practice of this invention use of a thermal displacement reaction is preferred as this avoids addition of another component (catalyst) to the reaction mixture.

Mild Oxidation

To convert the aluminum alkyl formed in the displacement reaction into aluminum alkoxide, a mild oxidation reaction is performed by contacting the product mixture with dry air or oxygen at a temperature in the range of about 30° to about 100° C., and preferably in the range of about 40° to about 60° C.). If oxygen is used it may be premixed or diluted with an inert gas such as argon, nitrogen, neon, krypton, or the like, or a mixture of air enriched with oxygen can be used. It is desirable to perform the reaction while agitating the reaction mixture to ensure intimate contact between the gas and liquid phases.

Hydrolysis

The hydrolysis reaction is best performed using an aqueous hydrolysis medium which can be simply plain water, or an alkaline or acidic aqueous system. Preferably, the beta-branched aluminum alkoxide formed in the oxidation step is hydrolyzed by use of a aqueous acid such as sulfuric or hydrochloric acid or an aqueous base such as aqueous sodium hydroxide solution. Temperatures are typically maintained within the range of about 40° to about 150° C., and preferably in the range of about 50° to about 100° C. Agitation of the mixture is desirable to ensure thorough contact between the aluminum alkoxide and the aqueous hydrolysis medium. The hydrolysis can be conducted before or after removal of the vinylidene olefin and deep internal olefin by distillation, although it is preferable to conduct this distillation before performing the hydrolysis. After a phase separation between the aqueous and organic phases, the recovered vinylidene alcohol can be purified by distillation, if desired.

The practice and advantages of this invention are further illustrated by the following illustrative examples wherein percentages are by weight unless otherwise specified. Examples 1–6 illustrate a sequence starting with 1-octene and trioctylaluminum.

EXAMPLE 1

Dimerization of 1-Octene

A total of 171.6 pounds (about 78 kg) of 1-octene is dimerized using 24.2 pounds (about 11 kg) of tri-n-octylaluminum. The reaction is performed by charging to a glass-lined reactor at room temperature maintained under a nitrogen blanket and equipped with a stirrer, 151 pounds of 1-octene, followed by 24.2 pounds of tri-n-octylaluminum, and finally by 20.6 pounds of 1-octene. Over a two-hour period the stirred mixture is heated from room temperature up to 165° C. Thereafter the stirred reaction mixture kept at 165°–170° C. for the duration of the reaction period. In a reaction conducted in this manner it was found that after 9 hours from the start of heating from room temperature, the 1-octene conversion (using hydrolyzed samples of the reaction mixture) was 94.6%, the selectivity to $C_{16}$ dimer was 91.7, and the purity of the $C_{16}$ vinylidene olefin was 93.0%.

EXAMPLE 2

Concurrent Displacement and Monomer Removal— Inert Gas Sweep

While purging the vapor space within a reactor with a nitrogen sweep, and without application of vacuum, a reaction mixture prepared as in Example 1 above is continuously stirred at 171° C. to effect concurrent displacement and removal of octene from the reaction mixture. After 3 hours at 171° C. following a 1-hour heat-up time from room temperature using 1.75 kg of reaction mixture formed as in Example 1. GC analysis of the product remaining in the reactor indicated that 6.7% (GC area %) of the hydrocarbon content was $C_8$ olefin and 90.3% (GC area %) was $C_{16}$ olefin. NMR analysis of the product indicated that 2.1 mol % was vinyl olefin and that 86 mol % was vinylidene olefin. After 19.5 at 171° C. hours these values were 0.2%, 96.4%, 0% and 90.1%, respectively.

EXAMPLE 3

Concurrent Displacement and Monomer Removal— Use of Vacuum

While continuously applying a vacuum in the range of 22 to 73 mm Hg, a reaction mixture prepared as in Example 1 above is continuously stirred at 171° C. for 2 hours to effect concurrent displacement and removal of octene from the reaction mixture. The reaction is more rapid than in Example 2. For example, after 0.75 hour (following a 0.75-hour heat-up time from room temperature) in a run performed in this manner using 1.85 kg of reaction mixture formed as in Example 1. GC analysis of the product remaining in the reactor indicated that 3.3% (GC area %) of the hydrocarbon product was $C_8$ olefin and that 92.4% (GC area %) of the hydrocarbon content of that mixture was $C_{16}$ olefin. NMR analysis indicated that 0.9 mol % of the hydrocarbon product was vinylolefin and 90.6 mol % was vinylidene olefin. After 2 hours at 171° C., these values were 1.3%, 94.5%, 0% and 89.7%, respectively.

EXAMPLE 4

Controlled Oxidation

Reaction mixture depleted in octene produced as in Example 2 or Example 3 initially at ambient temperature (28° C.) is sparged with dry air during for a period of 1 to 16.5 hours while allowing the temperature to rise adiabatically. The maximum temperature reached is about 54° C. Using a feed of 1.19 kg, analyses of hydrolyzed samples after 1 and 16.5 hours of air oxidation in this manner gave the results shown in Table I in which VdOH is vinylidene alcohol, DI olefin is deep internal olefin, Vd olefin is vinylidene olefin, and TS olefin is trisubstituted olefin.

TABLE I

| Component | After 1 hr, GC area % | After 16.5 hrs, GC area % |
|---|---|---|
| $C_8$ olefin | 0.05 | 0.18 |
| $C_{16}$ olefin | 80.04 | 76.66 |
| $C_{24}$ olefin | 2.40 | 2.40 |
| $C_{32}$ olefin | 1.09 | 3.13 |
| $C_{16}$ VdOH | 15.14 | 15.76 |
| Component | After 1 hr, % by NMR | After 16.5 hrs, % by NMR |
| DI olefin | 7.7 | 7.6 |
| Vd olefin | 73.1 | 65.2 |
| TS olefin | 1.2 | 8.0 |
| VdOH | 18.0 | 17.4 |

NMR analysis of the unydrolyzed product after 16.5 hours showed the ratio of beta-branched aluminum alkoxide to beta-branched aluminum alkyl (mol %) was 92.8% to 7.2%, respectively.

EXAMPLE 5

Recovery of $C_{16}$ Vinylidene Olefin by Distillation

Product formed as in Example 4 is subjected to distillation at 23 mm Hg and 175° C. to separate the $C_{16}$ vinylidene olefin from the aluminum alkoxide. A 1.17 kg batch of such product yielded 218 grams of bottoms and 733 grams of overhead. Table II shows the results of the GC analyses of the bottom and the overhead formed in this manner wherein the product mixture subjected to this distillation was the product of Example 4 after 16.5 hours of controlled oxidation.

TABLE II

| Component | Bottoms, GC area % | Overhead, GC area % |
| --- | --- | --- |
| $C_8$ olefin | 0.00 | 0.03 |
| $C_{16}$ olefin | 7.64 | 96.06 |
| $C_{24}$ olefin | 14.18 | 0.76 |
| $C_{32}$ olefin | 14.07 | 0.23 |
| $C_{38}$ olefin | 1.30 | 0.00 |
| $C_{16}$ VdOH | 62.80 | 2.91 |

EXAMPLE 6

Hydrolysis of Aluminum Alkoxide

The distillation residue (bottoms) from a distillation as in Example 5 is subjected to hydrolysis with dilute sulfuric acid at ambient temperature. The organic and aqueous phases are separated by decantation or other mechanical phase separation. Table III summarizes the GC analysis of the organic phase from the hydrolysis of the bottoms of Table II.

TABLE III

| Component | GC area % |
| --- | --- |
| $C_8$ olefin | 0.00 |
| $C_{16}$ olefin | 3.03 |
| $C_{24}$ olefin | 10.15 |
| $C_{32}$ olefin | 14.91 |
| $C_{34+}$ olefin | 1.70 |
| $C_{16}$ VdOH | 69.65 |

Example 7 illustrates a sequence starting with 1-hexene and tributylaluminum.

EXAMPLE 7

Using the procedure similar to that of Example 1, a feed of 149.8 pounds (about 67.9 kg) of 1-hexene is dimerized using 26.8 pounds (about 12.2 kg) of tri-n-butylaluminum by charging a mixture of tri-n-butylaluminum and 1-hexene in a molar ratio of 0.075, respectively, to a glass-lined reactor containing 1-hexene. Reaction temperature is 120° C. and the mixture is refluxed. The displacement reaction, conducted in similar fashion to Example 2, uses a temperature of 165° C. and a pressure of 0 to 10 psig with a nitrogen purge. Oxidation is effected using dry air diluted with dry nitrogen to 5 to 8% of oxygen. The vinylidene olefin is stripped off at 160° C. and 3 mm Hg for 1 hour. Hydrolysis is conducted at ambient temperature in 3 stages using a caustic wash followed by two water washes. The sequence results in the coproduction of vinylidene olefin and vinylidene alcohol as separate products.

Example 8 illustrates a sequence staging with 1-octene and trihexylaluminum.

EXAMPLE 8

Using procedures similar to Example 7 (except for use of a vacuum in the displacement stage), a feed of 170 pounds (about 77.1 kg) of 1-octene is dimerized using 37 pounds (about 16.8 kg) of tri-n-hexylaluminum by charging a mixture of tri-n-hexylaluminum and 1-octene in a molar ratio of 0.086, respectively, to a glass-lined reactor containing 1-octene. Reaction temperature is 165°–173° C. and the mixture is refluxed. The displacement reaction uses a temperature of about 160° C. and a reduced pressure of about 10 to about 30 mm Hg for 1 to 3 hours (note Example 3 above). Oxidation is effected using air diluted with dry nitrogen to 10% oxygen. Hydrolysis is conducted at ambient temperature in 2 stages using a caustic wash followed by a water wash.

Similar procedures can be used for producing vinylidene olefins and vinylidene alcohols from a mixture of 1-hexene and 1-octene to produce $C_2/C_{14}/C_{16}$ vinylidene olefins and $C_{12}/C_{14}/C_{16}$ vinylidene alcohols.

It is to be clearly understood and appreciated that in the specification and claims hereof all references to substances used in the process relate to the initial identity of the material being used and such references do not in any way require that during the process the substances must maintain that identity until the instant, if any, that a chemical transformation occurs to form a different substance. In short, once two or more of the identified materials are brought into contact with or proximity to each other, whether under reaction temperature conditions or not, one or more of them may undergo a change in identity as compared to their original identity, and such change or changes are intended to encompassed by the claims hereof as long as the end results of the overall process are in accordance with this invention.

This invention is susceptible to considerable variation in its practice. Therefore foregoing description is not intended to limit, and should not be construed as limiting, the invention to the particular exemplification as presented hereinabove. Rather, what is intended to be covered is as set forth in the ensuing claims and the equivalents thereof permitted as a matter of law.

What is claimed is:

1. A process for the coproduction of at least one vinylidene alcohol and at least one vinylidene olefin which comprises:

a) dimerizing one or more vinylolefins with an alkyl aluminum catalyst under dimerization conditions to form a first product mixture comprising at least vinylidene olefin and alkyl aluminum compound;

b) reacting vinylidene olefin with the alkyl aluminum compound under displacement conditions to form displaced 1-olefin and concurrently removing displaced 1-olefin from the displacement reaction mixture to form a second product mixture comprising at least beta-branched alkyl aluminum compound;

c) treating the second product mixture with air or oxygen under mild oxidation conditions to form a third product mixture comprising at least beta-branched aluminum alkoxide; and d) hydrolyzing the beta-branched aluminum alkoxide to form vinylidene alcohol.

2. A process according to claim 1 wherein the one or more vinylolefins dimerized in a) are linear 1-olefins having at least 4 carbon atoms per molecule.

3. A process according to claim 2 wherein the alkyl aluminum catalyst used in a) thereof is at least one linear alkyl aluminum catalyst.

4. A process according to claim 1 wherein the number of carbon atoms per alkyl group of the alkyl aluminum catalyst used in a) thereof corresponds to the number of carbon atoms in some or all of the vinylolefin being dimerized in a) thereof.

5. A process according to claim 1 wherein the alkyl aluminum catalyst is initially triethylaluminum.

6. A process according to claim 1 wherein the vinylidene alcohol is recovered.

7. A process according to claim 1 wherein the hydrolysis is effected using an aqueous acid or aqueous base as the hydrolysis medium.

8. A process according to claim 7 wherein the vinylidene alcohol is recovered from the hydrolysis medium by a phase separation.

9. A process according to claim 8 wherein the recovered vinylidene alcohol is purified by distillation.

10. A process according to claim 1 wherein the displacement conditions of b) thereof are thermal displacement conditions.

11. A process according to claim 1 wherein the vinylolefin being dimerized in a) thereof is a mixture comprising at least two vinylolefins, one of which has n carbon atoms and another of which has n+2 carbon atoms, where n is an integer in the range of from 3 to 34.

12. A process according to claim 11 wherein n is in the range of from 4 to 16.

13. A process according to claim 1 wherein the vinylolefin being dimerized in a) thereof is a mixture comprising at least two vinylolefins, one of which has n carbon atoms and another of which has n+1 carbon atoms, where n is an integer in the range of from 3 to 35.

14. A process according to claim 13 wherein n is in the range of from 4 to 17.

15. A process according to claim 1 wherein the vinylolefin being dimerized in a) thereof is a mixture comprising at least three vinylolefins, one of which has n carbon atoms, another of which has n+1 carbon atoms, and still another of which has n+2 carbon atoms, where n is an integer such that the sum of n+1 is at least 4 and not more than 36, and the sum of n+2 is at least 5 and not more than 36.

16. A process according to claim 15 wherein the sum of n+1 is at least 4 and not more than 18, and the sum of n+2 is at least 5 and not more than 18.

17. A process for the coproduction of at least one vinylidene alcohol and at least one vinylidene olefin which comprises:
   a) dimerizing one or more linear 1-olefins with an alkyl aluminum catalyst under dimerization conditions to form a first product mixture comprising (a) as dimerized products, vinylidene olefin and deep internal olefin, and (b) as other components, linear alkyl aluminum compound and monomeric olefin monomer;
   b) reacting the vinylidene olefin with the linear alkyl aluminum compound under displacement conditions to form displaced 1-olefin and concurrently removing displaced 1-olefin from the displacement reaction mixture to form a second product mixture comprising beta-branched alkyl aluminum compound, deep internal olefin and residual vinylidene olefin;
   c) treating the second product mixture with air or oxygen under mild oxidation conditions to form a third product mixture comprising beta-branched aluminum alkoxide, deep internal olefin and residual vinylidene olefin;
   d) distilling the third product mixture to recover vinylidene olefin and deep internal olefin;
   e) hydrolyzing the beta-branched aluminum alkoxide with an aqueous hydrolysis medium to form vinylidene alcohol, and recovering the vinylidene alcohol.

18. A process according to claim 17 wherein the one or more linear 1-olefins used in a) thereof have in the range of from 4 to about 18 carbon atoms per molecule.

19. A process according to claim 17 wherein the number of carbon atoms per alkyl group of the alkyl aluminum catalyst used in a) thereof corresponds to the number of carbon atoms in some or all of the vinylolefin being dimerized in a) thereof.

20. A process according to claim 17 wherein the alkyl aluminum catalyst is initially triethylaluminum.

21. A process according to claim 17 wherein the linear 1-olefin being dimerized a single 1-olefin having in the range from 4 to about 14 carbon atoms in the molecule.

22. A process according to claim 17 wherein the linear 1-olefin being dimerized is a mixture of at least two 1-olefins having in the range from 4 to about 14 carbon atoms in the molecule.

23. A process according to claim 17 wherein the vinylidene alcohol is recovered from the hydrolysis reaction mixture by a phase separation.

24. A process according to claim 17 wherein said aqueous hydrolysis medium is an aqueous acid or aqueous base hydrolysis medium.

25. A process according to claim 17 wherein the recovered vinylidene alcohol is purified by distillation.

26. A process according to claim 17 wherein the displacement conditions of b) thereof are thermal displacement conditions.

27. A process according to claim 17 wherein:
   A) the vinylolefin being dimerized in a) thereof consists essentially of a single linear 1-olefin having from 4 to about 24 carbon atoms in the molecule;
   B) the alkyl aluminum catalyst is initially triethylaluminum;
   C) the displacement conditions of b) thereof are thermal displacement conditions;
   D) the aqueous hydrolysis medium is an aqueous acid or aqueous base hydrolysis medium; and
   E) the vinylidene alcohol is recovered from the hydrolysis reaction mixture by a phase separation.

28. A process according to claim 17 wherein:
   the vinylolefin being dimerized in a) thereof is a mixture comprising at least two vinylolefins, one of which has n carbon atoms and another of which has n+2 carbon atoms, where n is an integer in the range of from 3 to 34;
   B) the alkyl aluminum catalyst is initially triethylaluminum;
   C) the displacement conditions of b) thereof are thermal displacement conditions;
   D) the aqueous hydrolysis medium is an aqueous acid or aqueous base hydrolysis medium; and
   E) the vinylidene alcohol is recovered from the hydrolysis reaction mixture by a phase separation.

29. A process according to claim 17 wherein:
   A) the vinylolefin being dimerized in a) thereof is a mixture comprising at least two vinylolefins, one of which has n carbon atoms and another of which has n+1 carbon atoms, where n is an integer in the range of from 3 to 35;
   B) the alkyl aluminum catalyst is initially triethylaluminum;
   C) the displacement conditions of b) thereof are thermal displacement conditions;
   D) the aqueous hydrolysis medium is an aqueous acid or aqueous base hydrolysis medium; and
   E) the vinylidene alcohol is recovered from the hydrolysis reaction mixture by a phase separation.

30. A process according to claim 17 wherein:

A) the vinylolefin being dimerized in a) thereof is a mixture comprising at least three vinylolefins, one of which has n carbon atoms, another of which has n+1 carbon atoms, and still another of which has n+2 carbon atoms, where n is an integer such that the sum of n+1 is at least 4 and not more than 36, and the sum of n+2 is at least 5 and not more than 36;

B) the alkyl aluminum catalyst is initially triethylaluminum;

C) the displacement conditions of b) thereof are thermal displacement conditions;

D) the aqueous hydrolysis medium is an aqueous acid or aqueous base hydrolysis medium; and E) the vinylidene alcohol is recovered from the hydrolysis reaction mixture by a phase separation.

* * * * *

UNITED STATES PATENT AND TRADEMARK OFFICE
CERTIFICATE OF CORRRECTION

PATENT NO. : 5,731,480  
DATED : March 24, 1998  
INVENTOR(S) : Lin

Page 1 of 2

It is certified that error appears in the above-identified patent and that said Letters Patent is hereby corrected as shown below:

On the title page, under item [56] References Cited, insert the following:

U. S. PATENT DOCUMENTS

| EXAMINER INITIAL | PATENT NUMBER | ISSUE DATE | PATENTEE | CLASS | SUBCLASS | FILING DATE IF APPROPRIATE |
|---|---|---|---|---|---|---|
|  | 3 3 9 1 1 7 5 | 7/68 | Davis |  |  |  |
|  |  |  |  |  |  |  |

UNITED STATES PATENT AND TRADEMARK OFFICE
CERTIFICATE OF CORRRECTION

PATENT NO. : 5,731,480  
DATED : March 24, 1998  
INVENTOR(S) : Lin

Page 2 of 2

It is certified that error appears in the above-identified patent and that said Letters Patent is hereby corrected as shown below:

On the title page, under item [56] References Cited, insert the following:

FOREIGN PATENT DOCUMENTS

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 1 | 0 | 2 | 6 | 6 | 8 | 6 | 4/66 | Great Britain | | | | |
| | | 1 | 3 | 7 | 8 | 0 | 2 | 7 | 10/64 | France | | | | |
| | | 0 | 5 | 7 | 4 | 8 | 5 | 4 | 12/93 | European | | | | |
| | | | | | | | | | | | | | | |

Signed and Sealed this

Thirteenth Day of April, 1999

Attest:

Q. TODD DICKINSON

*Attesting Officer*   *Acting Commissioner of Patents and Trademarks*